(12) United States Patent
Ho

(10) Patent No.: US 6,949,377 B2
(45) Date of Patent: Sep. 27, 2005

(54) CHEMILUMINESCENCE-BASED MICROFLUIDIC BIOCHIP

(76) Inventor: Winston Z. Ho, 14541 Langhill Dr., Hacienda Heights, CA (US) 91745

( * ) Notice: Subject to any disclaimer, the term of this patent is extended or adjusted under 35 U.S.C. 154(b) by 561 days.

(21) Appl. No.: 10/022,007

(22) Filed: Dec. 13, 2001

(65) Prior Publication Data

US 2002/0123059 A1 Sep. 5, 2002

Related U.S. Application Data

(60) Provisional application No. 60/273,077, filed on Mar. 5, 2001.

(51) Int. Cl.[7] ............................ C12M 1/34; C12Q 1/68; G01N 33/53; G01N 15/06; G01N 21/64
(52) U.S. Cl. ...................... 435/287.1; 435/6; 435/7.1; 435/287.2; 422/68.1; 422/82.05
(58) Field of Search ................................ 435/6.1, 91.1, 435/183, 283.1, 287.1, 287.2, 287.3, 288.4, 288.5, 292.1; 422/50, 68.1, 82.05, 82.07, 201; 530/300, 350; 536/23.1; 424/130.1, 184.1

(56) References Cited

U.S. PATENT DOCUMENTS

| 4,426,451 | A |   | 1/1984  | Columbus |
|-----------|---|---|---------|----------|
| 4,690,899 | A |   | 9/1987  | Klose et al. |
| 4,710,472 | A |   | 12/1987 | Saur |
| 5,096,669 | A |   | 3/1992  | Lauks |
| 5,164,598 | A |   | 11/1992 | Hillman et al. |
| 5,229,297 | A |   | 7/1993  | Schnipelsky |
| 5,585,069 | A | * | 12/1996 | Zanzucchi et al. .......... 422/100 |
| 6,018,387 | A |   | 1/2000  | Eppler |
| 6,132,685 | A | * | 10/2000 | Kercso et al. ............... 422/104 |
| 6,168,948 | B1 | * | 1/2001 | Anderson et al. ......... 435/287.2 |
| 6,186,660 | B1 |   | 2/2001 | Kopf-Sill |
| 6,187,267 | B1 |   | 2/2001 | Taylor |
| 6,238,538 | B1 |   | 5/2001 | Parce |

(Continued)

FOREIGN PATENT DOCUMENTS

EP    1203959 A1    5/2002

OTHER PUBLICATIONS

Stanley Abramowitz, "DNA Analysis in Microfabricated Formats", Journal of Biomedical Microdevices, 1:2, 107–112 (1999).

(Continued)

Primary Examiner—Kenneth R. Horlick
Assistant Examiner—Frank W Lu
(74) Attorney, Agent, or Firm—Liu & Liu

(57) ABSTRACT

The disclosure describes how to use luminescence detection mechanism, move microfluid, and control multiple-step biochemical reactions in closed confined microfluidic biochip platform. More particularly, a self-contained disposable biochip with patterned microchannels and compartments having storage means for storing a plurality of samples, reagents, and luminescent substrates. At least one external microactuator in the biochip system produces positive pressure and automates multiple-step reactions in microfluidic platforms for clinical chemistry, cell biology, immunoassay and nucleic acid analysis. The method comprises the steps of transferring sequentially at least one of samples, reagents, and then luminescent substrate from compartments through microchannels to reaction sites. The luminescent substrates react with probes to form a probe complex resulting into luminescence, which is detected by an optical detector.

11 Claims, 3 Drawing Sheets

U.S. PATENT DOCUMENTS

| | | |
|---|---|---|
| 6,242,246 B1 | 6/2001 | Gold |
| 6,268,219 B1 | 7/2001 | McBride |
| 6,270,641 B1 | 8/2001 | Griffiths |
| 6,271,042 B1 | 8/2001 | Watson, Jr. |
| 6,300,138 B1 | 10/2001 | Gleason et al. |
| 6,379,929 B1 * | 4/2002 | Burns et al. ............... 435/91.2 |
| 6,429,025 B1 | 8/2002 | Parce et al. |
| 2002/0124879 A1 | 9/2002 | Kaplan et al. |
| 2002/0187560 A1 | 12/2002 | Pezzuto et al. |

OTHER PUBLICATIONS

Mark J. Feldstein, et al., "Array Biosensor: Optical and Fluidics Systems", Journal of Biomedical Microdevices, 1:2, 139–153 (1999).

Irina Kleps, et al., New Micro– and Nanoelectrode Arrays for Biomedical Applications, Journal of Biomedical Microdevices, 3:1, 29–33 (2001).

International Search Report of Counterpart PCT Application No. PCT/US04/00768.

* cited by examiner

Before Actuation

Before Actuation

CHEMILUMINESCENCE-BASED MICROFLUIDIC BIOCHIP

RELATED APPLICATION

The present application claims the benefit of 35 U.S.C. 111(b) Provisional applications Ser. No. 60/273,077 filed Mar. 5, 2001 entitled "Chemiluminescent biochip apparatus and method".

FIELD OF THE INVENTION

The invention is related to microfluidic biochip devices that utilize chemiluminescence or bioluminescence detection mechanism to rapidly detect chemical and biological species, for example cardiac markers, cancer marker, infectious diseases, gene diseases and mutation, nucleic acids, hormones, HIV, bacteria, and many other biological analytes with very high sensitivity. Apparatus and methods thereof are disclosed for analyzing biological samples in a self-contained biochip platform for luminescence-based immunological and nucleic acids analyses.

BACKGROUND OF THE INVENTION

Light-emitting chemical reactions (chemiluminescence, CL) and light-emitting biological reactions (bioluminescence, BL) have a diverse range of analytical applications. Advantages of CL and BL assays include high sensitivity due to enzyme amplification, rapid signal generated in a few seconds, and assays do not need an external excitation light source. In many situations, these procedures are replacing the use of radioactive nuclides. As luminescent agents have become more efficient, many more studies are making use of luminescence assays as analytical tools. Chemiluminescent substrates, such as dioxetane, luminol, acridinium ester and hydrazide, have been developed. These compounds are catalyzed by hydrolytic enzyme and the resulting products emit light. Bioluminescent reactions are generally more efficient than chemiluminescence. BL has traditionally been associated with firefly luciferase. AquaLite (SeaLite Sciences, Ga.) is a recombinant form of a photoprotein from jellyfish. It can be triggered to produce all of its light in a single step within a few seconds. CL and BL methods have been developed for many enzyme labels (alkaline phosphatase, galactosidase, horseradish peroxidase, etc.). The enzymes are conjugated to the secondary antibody or analytes for subsequent substrate reactions. In a typical sandwich immunoassay, the analyte is sandwiched between the antibody conjugate and immobilized probes. The luminescence intensity at any time is a direct measure of the concentration of enzyme conjugate or analyte for positive identification. The newly developed dioxetane offers a detection sensitivity of 600 molecules ($10^{-21}$ mole), making it several orders more sensitive than the fluorescence-based assay. Rather than a luminescent species being directly attached to a target analyte or to its binding partner, an enzyme is used to catalyze a luminescent reaction. The catalytic turnover ability of the enzyme allows thousands of potentially luminescent reactions to occur per second as long as sufficient substrate is present. Less than $10^{-21}$ mole of alkaline phosphatase can be detected in solutions using dioxetane-based compound, such as Lumi-PPD and Lumi-PS-1 of Lumigen Inc. (Southfield, Mich.). When Lumi-PPD is added to a microwell containing alkaline phosphatase, the resulting chemiluminescence reaches a maximum after 5–10 minutes and remains constant for more than an hour. Various luminescence detection devices (for example, luminometers) are commercially available. U.S. Pat. No. 6,018,387 discloses a method with an optical reflector to increase luminescence collection efficiency in a luminometer system and U.S. Pat. No. 6,187,267 addresses a free-space luminometer with a confocal optical array to detect an array of samples. No microfluidic system has been disclosed in luminometer patents.

Numerous immunoassay and nucleic acid assays, such as RIA, ELISA, fluorescence, polarization, and chemiluminescence, have been developed to varying degrees based on instrumental or visual inspection of results. Three common methods include: First, the dip-stick (membrane strip): the pregnancy test is a typical example. While such tests have proven useful in obtaining qualitative results based on the determination of analyte, they are not very useful for making quantitative measurement, especially with whole blood or in disease diagnoses requiring high sensitivity. Second, the modular cluster systems can run up to several thousands of samples per day. These modular workstations with robotic liquid handlers have the capability of running 200–800 tests per hour in hospitals and clinical laboratories. They often operate in a batch mode after a large collection of sample. These systems are too large to be used for near-patient-site tests. Third type is the point-of-care testing (POCT) device. Many hospitals have started to set up POCT training program for nurses and clinicians. I-Stat has a hand-held POCT device, described in U.S. Pat. No. 5,096,669, with a small cartridge for measuring the "chemical" components (blood gas, pH, sodium, potassium, etc.) in blood samples. The system based on one-step conductivity measurement and is very easy to use. Therefore, it is desirable to have microfluidic-based POCT for immunoassay (bacteria, virus, protein, hormone, cell receptor, etc.) and nucleic acid analysis (gene mutation, gene expression, oligonucleotide, DNA, RNA, single nucleotide polymorphism, etc.). However, immunoassay and nucleic acid assays often require multiple-step of reactions. Automating multiple-step reactions in a microfluidic biochip platform have been very challenging.

Nucleic acid analysis has been known to produce very sensitive testing results. The quantity of the analyte in the sample is very small. Polymerase Chain Reaction (PCR), U.S. Pat. No. 5,229,297, technique provides a high level of sensitivity, but it takes 20–40 thermal cycles and 2–4 hours to prepare the sample and amplify nucleic acid samples. Most DNA chips are based on PCR amplification, it is too time consuming for POCT application. "Laboratory on a chip" technologies, as disclosed in U.S. Pat. No. 6,238,538 and No. 6,270,641, are based on the electro-osmosis mechanism for nucleic acid electrophoresis. U.S. Pat. No. 6,271,042 utilizes a biochip structure with CCD camera for fluorescence detection. U.S. Pat. No. 6,215,894 discloses a method to process the biochip image. U.S. Pat. No. 6,242,246 describes a method to detect nucleic acids in a biochip platform based on nucleotide affinity reactions. None of the microfluidic biochip is based on non-PCR chemiluminescence detection.

CL and BL are used to detect nucleic acids using the binding nature of double strand oligonucleotides. Oligonucleotide probes hybridize with samples or conjugated (biotinylated) oligonucleotides on solid surfaces. The biotinylated oligonucleotides can easily bind to streptavidin-enzyme conjugate with very high affinity. Consequently, enzyme conjugates can trigger luminescence substrate to produce light as that occurred in chemiluminescent immunoassay. Instead the sensitivity of the reaction is judged by amplification of a signal. Since there are no thermal cycles involved in DNA analysis, the consequence of crosscontamination between samples is reduced when compared to PCR. The luminescence is also applied to the recently developed branched DNA (bDNA) assay. The concept of branched DNA is derived from the assembly of structural components in all biological systems. DNA possesses a well-known structure, which is invariant to sequence. The predictability of the association of DNA's cohesive ends, is the basis for genetic engineering endeavors that underlie modern molecular biology. DNA molecules with single-strand "sticky" ends are used to direct the assembly of individual fragments in a particular order. The predictability of sticky-ended ligation extends to the geometry of the product. Therefore, it is possible to design oligonucleotide sequences of DNA that will self-assemble to form stable branched complexes. A DNA branch junction has been built with as many as six double helical arms. The bDNA assay requires minimal sample preparation, allowing for rapid or point-of-care testing. Based on the double amplification principle, branched DNA multimer and enzyme chemiluminescence, the biochip provides microfluidics for all necessary nucleic acid chemistries. The advantage of the microfluidic biochip system is to automate the delivery of samples, hybridized amplifiers, enzyme conjugates, chemi-luminescence substrates, and washing solutions to a reaction site in a predetermined order. After hybridization of enzyme-labeled probes with the amplifiers, the oligonucleotide-probe complex is detected by use of a chemiluminescence substrate. Branched DNA kit, commercialized by Bayer Diagnostics, is a clear deviation from PCR amplification technologies because the target nucleic acid is not replicated. The combination of bDNA luminescence and automated microfluidic biochip not only provides high sensitivity, but also offers simple and rapid testing.

The establishment of miniaturized microfluidic systems has brought to the immediate horizon the possibility of point-of-care analysis, to be achieved by extremely fast, hand-held, or portable laboratories. Many firms and research institutes are actively engaged in developing microfluidics and microarray technologies. Although significant efforts have been put into the development, most biochips are not self-contained; therefore, external reservoirs are used to store the reagents. When a biochip is connected to external reservoirs, it requires pumps and tubes. The resulting system becomes too large and too complex for POCT applications.

Prior to this invention, POCT devices are commonly lack of sensitivity. No system demonstrates the same performance: sensitivity, reliability, and precision as large stand-alone or modular systems. In combination of microactuator, microfluidic biochip, and highly sensitive luminescence detection mechanism, POCT devices can achieve same performance as the large workstations.

SUMMARY OF THE INVENTION

The invention is to integrate a highly sensitive luminescence assay protocol into a miniaturized self-contained biochip and apparatus. No bulking elements, such as external reagent reservoirs, pumps, and tubes, are necessary. Because all reagents are self-contained in closed confinement, no environmental contaminants will occur during the multiple steps of operation.

It is an object of the present invention to provide automated luminescence biochip devices that using microfluidics to perform all necessary reaction steps. Loading sample is the only required human involvement. Ease of use is one of the main purposes of the device.

One of the objects of the present invention is to provide biochip system for analyzing biological fluids, in particularly for clinical chemistry, immunoassay and nucleic acid analysis. Because of the sample and reagents are stored inside the sealed compartment, it is possible for long-term storage. In accordance with this aspect of the invention, an external microelectro-actuator situated above the disposable biochip is used to produce the positive pressure, open up the compartment, transport the fluids, and control the biochemical reactions. The invention is to provide the method of using microfluidic biochip-based devices for simple, rapid, or POCT application.

It is also an object of the present invention to provide microactuator arrays for manipulating high density of microfluidic arrays on a biochip. In accordance with this aspect of the invention, actuators in an array are in alignment with the sample and reagent cavities. It has long been appreciated that a disposable biochip should be very low cost. Therefore, no active mechanism should be fabricated on the chips. Multiple analytes can be tested on the same biochip. Only minimal amount of samples is needed for microfluidic biochip platform.

It is also an object of the present invention to provide high density biological probes immobilized on a plurality of spots on at least one of said reaction site. Therefore, one sample can be simultaneously tested for multiple analytes on the same reaction site.

The present invention has the advantage of automating multiple steps luminescence bioassay, and providing accurate and reproducible results. It should be understood, however, that the detail description and specific examples, while indicating preferred embodiments of the present invention, are given by way of illustration and not of limitation. Further, as is will become apparent to those skilled in the area, the teaching of the present invention can be applied to devices for measuring the concentration of a variety of body fluidic samples.

DETAILED DESCRIPTION OF EMBODIMENTS OF THE INVENTION

Figure 1:
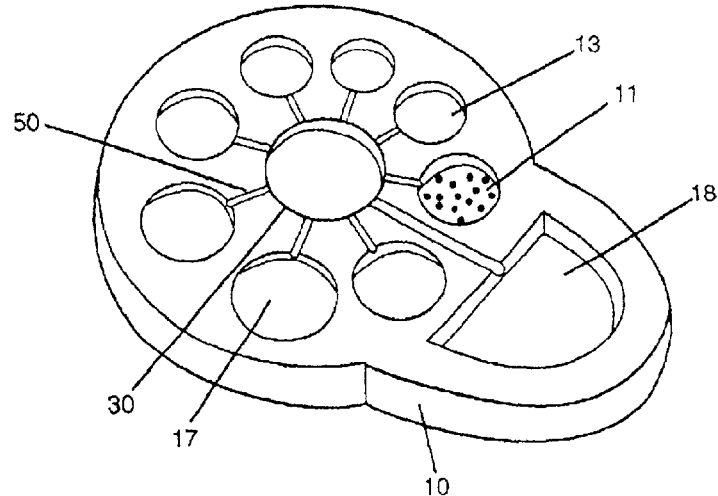
FIG. 1 is a perspective view of luminescence-based microfluidic biochip. Depending on the assay protocol, the biochip has storage means for a plurality of samples, reagents, luminescent substrates, and reaction sites immobilized with probes.

The invention is hereinafter described primarily with respect to the use of automatic microfluidic biochip technology and chemically or biologically triggered luminescence to provide amplified signal for biological analyte detection. The example shown in FIG. 1 is a self-contained microfluidic-based luminescence biochip that is formed by bounding layers of polymer materials with patterned compartments and microchannels. The biochip 10 has a plurality of compartments and interconnecting microchannels 50, a dimension between 10 μm–3 mm, and the compartments having storage means for a plurality of samples 11, reagents 13, luminescent substrates 17, reaction site 30, and waste 18. The sample is selected from a group consisting of proteins, antibodies, antigens, hormones, biological cells, and nucleic acids. The reagents are enzyme conjugates (enzyme labeled -antibody, -antigen, -oligonucleotide, -proteins, -streptavidin, etc.), washing buffers, bDNA amplifier, dilution buffers, and other materials required in assay protocols. A predetermined amount of the reagents, 100 nl–500 μl in volume, are stored inside the compartments. The reagents can be dry agents too. In case of dry reagent is used, the dilution buffers will be transported to the dry agent compartment to form liquid solution. The prepackage reagents are sealed inside the compartments. The biochip is designed to be a disposable or one-time use cartridge. The chip can be mass-produced using injection molding. The common plastic chip materials used are polystyrene, polycarbonate, polypropylene, or polydimethysiloxane (PDMS). Depending on assay protocol, an array of patterns can be designed for analyzing multiple samples or multiple analytes on the same chip.

Figure 2:
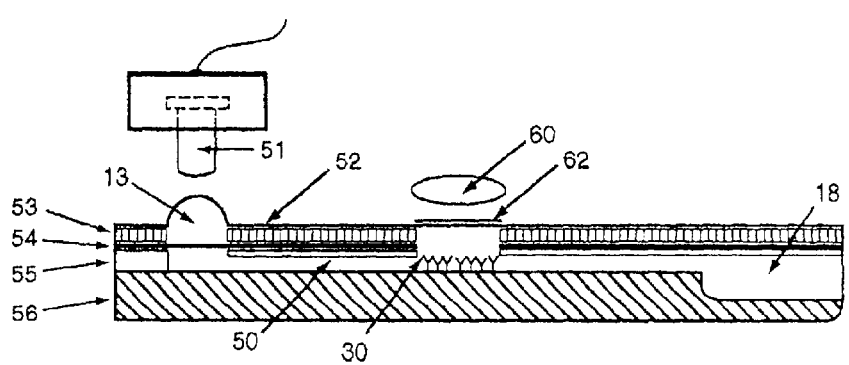
FIG. 2 is the cross-section view of the microactuator and biochip. The microactuator is used to control fluid mixing and movement. Each reagent is sealed in a thin plastic compartment. Before (top portion) and after (bottom portion) the reagent is released from the compartment and into microchannels.
Figure 2:
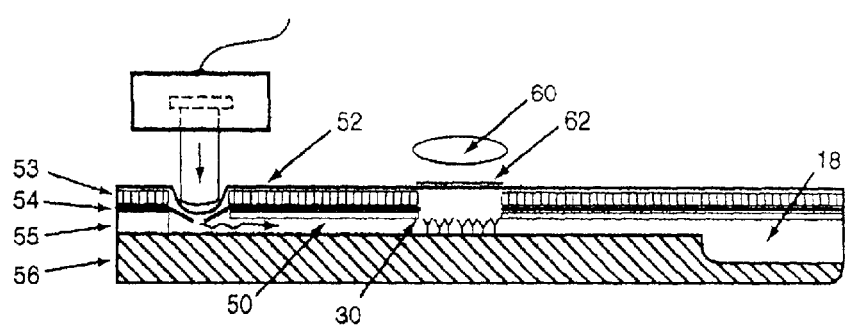

The methods to move microfluid in the biochip platform are commonly performed by electro-osmotic, capillary, piezoelectric, vacuum, and microactuator. The example shown in FIG. 2 is a biochip system utilizes external microactuator 51 to sequentially transfer at least one of samples and then at least one of reagents through microchannels to at least one of reaction sites. No on-chip pump is required. There are many ways to form compartments and microchannels in a biochip. For example, the chip can be fabricated with five layers structure: a plastic compartment plate 53, a microchannel plate 55, a chip plate 56, and two thin films. The reagent compartment 13 is sandwiched between a top thin film 52 and a bottom thin film 54, which are used to seal the compartments and prevent the liquid leakage. The bottom thin film 54, a few micrometers thick, is made of breakable material and is a barrier between a compartment and a microchannel. The microactuator is located above the chip set. The microactuator is designed specially for drop-on demand application. When the actuator is initiated, it collapses the bottom layer 54 of the compartment, and causes the solution to flow out of the compartment, into the microchannel 50, and then into the reaction sites 30. Fluid movement occurs by a positive pressure generated by the actuator's mechanical movement. The top layer 52 will remain collapsed and thus prevents fluid from moving back during later operation. Either array of actuators or an actuator on translation stage can be arranged to locate above a particular compartment. All the automated processes are controlled by a microprocessor. It is also feasible to construct a rotating chip-type disk using a micro-gear to accurately position the actuator head on the top of the compartments.

An optical detector 60, located above or under reaction sites, is used for detecting luminescence generated from the luminescent probe complex. Various optical detectors, such as photodiode, charge-coupled device (CCD), photomultiplier tube (PMT), or photon counting detector, have different degree of sensitivity. PMT and photon counting detectors can achieve an electronic amplification factor as high as $10^6$–$10^8$. Conventional PMTs require a ~1 kV power source, but new miniaturized detector requires only a 5 V. Most of the chemiluminescence emission wavelengths are in the visible region. A narrow-band optical filter 62 ensures detecting luminescence wavelengths. The system is integrated with a microactuator, detector, microprocessor, electronics, a display, and translation stage. The translation stage can position a particular chip compartment under a particular microactuator or above the detector. With additional focus lens, the detector can scan and measure luminescent signals from various spots on a reaction site. The output of the detector is interfaced to an analog to digital converter and a microprocessor to calculate analyte concentration.

Figure 3:
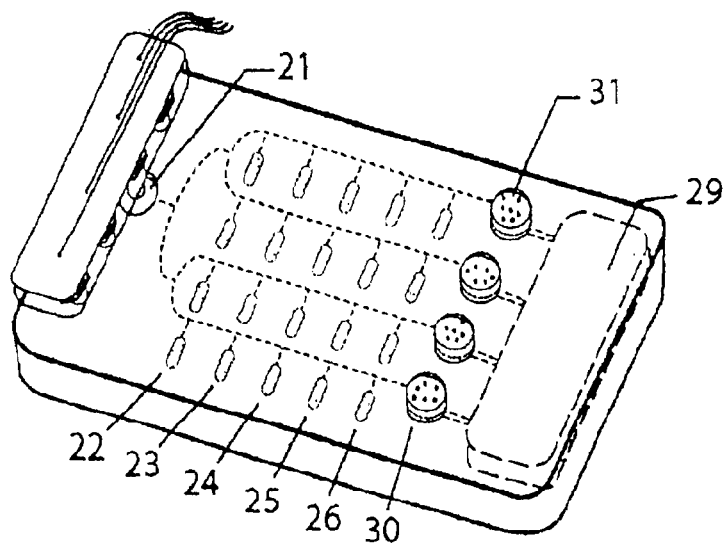
FIG. 3 is a perspective view of a luminescence-based microfluidic biochip with microfluidic circuitry for a typical sandwiched immunoassay.

There are many biological assay formats. Sandwiched assay is a common format. FIG. 3 shows a self-contained microfluidic-based luminescent biochip based on sandwiched immunoassay for multiple analytes assay. All compartments are connected to the reaction site 30. The compartments store samples 21, washing buffers 22, 24, and 25, enzyme conjugate 23, and CL substrate 26. After sequentially transfer samples, antibody conjugate, luminescence substrate, and many washing solutions to the reaction site, if the reaction is positive, a sandwiched complex will be formed at reaction sites. The analyte-specific antibody probe 31 at the reaction site 30 is responsible for capturing the antigen, while the labeled antibody is used to report and signal antibody-antigen complex formation by subsequent chemiluminescent substrate reaction. The enzyme conjugate can be either a polyclonal antibody or monoclonal antibody labeled with an enzyme, such as alkaline phosphatase or horseradish peroxidase. Multiple washing buffers may be needed to wash away the un-bounded materials and thus minimize the background signal. All wastes are flown to the waste compartment. At the waste compartment, a hydrophobic vent is used to release air, but not liquid. This micro vent prevents back streaming of reagents. The luminescent intensity at any point in time on the rising or plateau portion of the curve is a direct measurement of the amount of the analyte. The chip pattern can be modified for competitive immunoassay. The same principle is applicable to nucleic acids assay.

Figure 4:
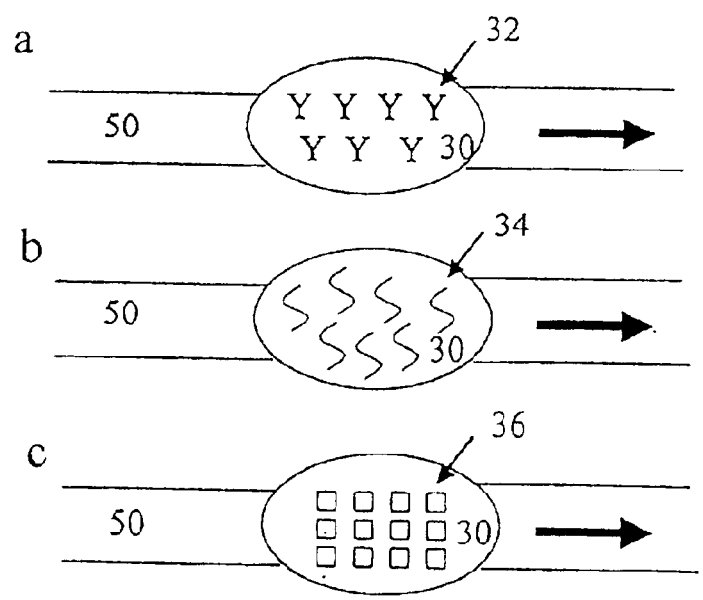
FIG. 4 is a perspective view of the reaction site immobilized with (a) antibody, (b) oligonucleotide, and (c) high density of biological probes at a plurality of spots as capture probes in the microfluidic system. The biological probes can be used to catch different analytes in the samples.

The probes may be selected from a group consisting of proteins, antibody, antigen, biological cells, and oligonucleotides. FIG. 4 shows the immobilization of probes: (a) antibody 32, (b) oligonucleotide 34, and (c) high density of multiple biological probes 36 on a plurality of spots at reaction sites 30. The density of multiple probes can be very large depends on the size of each spot. For a 50 μm×50 μm spot, it can easily reach more than 10,000 spots on a 1 cm×1 cm reaction area. It provides the potential for simultaneous high throughput screening. There are two immobilization methods. Physical adsorption is the most common method for immobilizing proteins and oligonucleotides on polystyrene-based 96-well microplates. Chemical adsorption methods, such as biotinylated antibody to the activated surface (treated with hydroxysuccinimide), are used to ensure long-term stability and minimize non-specific binding. The functional groups on proteins, the receptors on cell membranes, antibody-antigen reaction, and the double strands character of oligonucleotides are the basic capture mechanisms for probe-target reactions.

Once all reagents are prepared in the compartments, an immunoassay protocol is described at follow: the only step for the operator is to inject a few microliters sample into a compartment 21. Then, the system will automatically 1. Initiate the assay by moving the sample from compartment 21 into the reaction site 30 immobilized with the analyte-specific antibody and incubate for 5 minutes;

2. Dispense washing or diluting solution in compartment 22 into the reaction site, and to remove the unbound analyte;
3. Move the anti-analyte enzyme conjugate from compartment 23 to the reaction site and incubate for 5 minutes;
4. Wash reaction site twice with wash buffers from compartments 24 and 25, to remove the unbound anti-analyte conjugate;
5. Deliver chemiluminescence substrate from compartment 26 into the reaction site; and
6. The reaction of CL substrate and probe complexes generating luminescence. The intensities are recorded for a certain period of time.

Figure 5A:
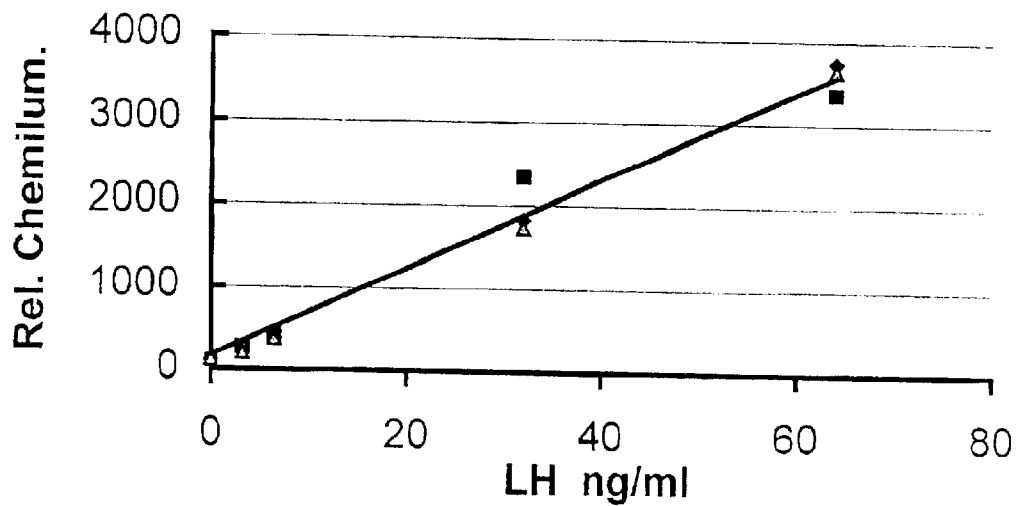
FIG. 5 show two examples of assay-linearity studies with the microfluidic biochip system for (a) luteinizing hormone, and (b) troponin I cardiac marker tests.
Figure 5B:
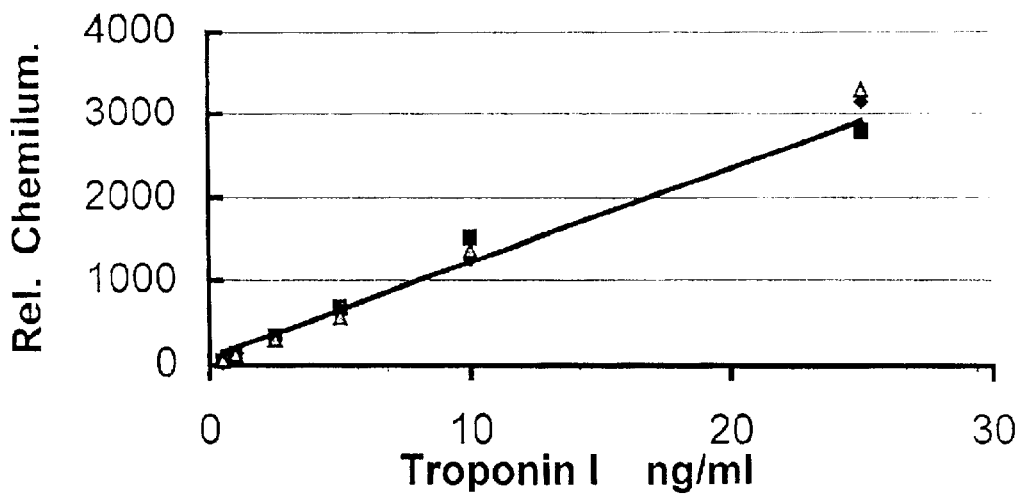

FIG. 5(a) shows the test results, which plots light intensity versus a series of analyte concentrations, for luteinizing hormone (LH) based on chemiluminescent biochip sandwiched immunoassay. The LH with the concentration of 0, 5, 15, 50, and 100 mIU/ml correspond to the concentrations of 0, 3.2, 6.4, 32, and 64 ng/ml (1 mIU/ml of LH is equal to 0.64 ng/ml.). The response curve shows a linear regression, $Y=53.2X+177$ with a coefficient of linear regression $R^2=0.968$. X is the concentration of LH in the unit of ng/ml. Based on our preliminary experiments we obtained a detection limit of 20 pg/ml for LH. Considering the total analyte used was 25 $\mu$l it is equivalent to $5 \times 10^{-18}$ mole or five attomoles LH. FIG. 5(b) plots light intensity versus a series of analyte concentrations for troponin I. A series of CTn I (0, 0.5, 1, 2.5, 5, 10, and 25 ng/ml) was prepared to cover the clinically significant dynamic range. The resulting response curve shows a linear regression, $Y=112.6X+99.9$ with a coefficient of linear regression $R^2=0.979$. Based on these experiments, a detection limit of 50 pg/ml for troponin I was obtained.

The claim of the invention is:

1. A method for performing biological assay in a self-contained microfluidic-based luminescence biochip, the method comprising the steps of:

(a) providing said biochip with a plurality of compartments and interconnecting microchannels, said compartments having storage means for storing a plurality of samples, reagents, luminescent substrates, and reaction sites immobilized with probes; and means for interconnecting said compartments to provide fluid transfer through said microchannels;

(b) transferring sequentially at least one of said samples and then at least one of said reagents through said microchannels to at least one of said reaction sites, said at least one sample and said at least one reagent reacting with said probes and forming a probe complex;

(c) transferring said luminescent substrate through said microchannels to said reaction sites, said luminescent substrates reacting with said probe complex and generating luminescence; and (d) detecting said luminescence with an optical detector located above or under said reaction sites.

2. The method as defined in claim 1, wherein said compartments further include washing buffers, the method further including a step prior to said step (c), said step comprising transferring said washing buffers through said microchannels to said reaction sites and washing away an excessive and un-reacting portion of said samples or said reagents.

3. The method as defined in claim 1 or 2, wherein one of said luminescent substrates is a chemiluminescent material or a bioluminescence material.

4. The method as defined in claim 1 or 2, wherein one of said reagents is an enzyme conjugate.

5. The method as defined in claim 1 or 2, wherein at least one of said samples is selected from a group consisting of proteins, antibodies, antigens, hormones, biological cells, and oligonucleotides.

6. The method as defined in claim 1 or 2, wherein one of said reagents is a branched DNA amplifier adapted for luminescence signal amplification.

7. The method as defined in claim 1 or 2, wherein means for interconnecting said compartments to provide fluid transfer is based on an external microactuator positioned above said compartments.

8. The method as defined in claim 1 or 2, wherein said microchannels have a dimension between 10 $\mu$m–3 mm.

9. The method as defined in claim 1 or 2, wherein said compartments have a volume between 100 nl–500 $\mu$l.

10. The method as defined in claim 1 or 2, wherein said compartments formed by thin film materials.

11. The method as defined in claim 1 or 2, wherein one of said reagents is dry reagent.

* * * * *

UNITED STATES PATENT AND TRADEMARK OFFICE
CERTIFICATE OF CORRECTION

PATENT NO. : 6,949,377 B2
DATED : September 27, 2005
INVENTOR(S) : Winston Z. Ho It is certified that error appears in the above-identified patent and that said Letters Patent is hereby corrected as shown below:

Column 8,
Line 43, add claim -- 12. The method as defined in claim 1 or 2, wherein at least one of said biological probes is selected from a group consisting of proteins, antibodies, antigens, hormones, biological cells, and nucleic acids. --.
Line 45, add claim -- 13. The method as defined in claim 10, wherein said biological probes are immobilized on a plurality of spots on at least one of said reaction sites. --.

Signed and Sealed this

Sixth Day of December, 2005

JON W. DUDAS
*Director of the United States Patent and Trademark Office*